United States Patent [19]

Hsu et al.

[11] Patent Number: 5,776,451
[45] Date of Patent: Jul. 7, 1998

[54] USE OF INTERLEUKIN-10 IN ADOPTIVE IMMUNOTHERAPY OF CANCER

[75] Inventors: Di-Hwei Hsu, Mountain View; Kevin W. Moore; Hergen Spits, both of Palo Alto, all of Calif.

[73] Assignee: Schering Corporation, Kenilworth, N.J.

[21] Appl. No.: 270,805

[22] Filed: Jul. 5, 1994

Related U.S. Application Data

[63] Continuation of Ser. No. 995,564, Dec. 23, 1992, abandoned, which is a continuation of Ser. No. 830,493, Feb. 4, 1992, abandoned, which is a continuation of Ser. No. 641,342, Jan. 16, 1991, abandoned.

[51] Int. Cl.$^6$ .................................................. A61K 45/05
[52] U.S. Cl. ........................ 424/85.2; 424/85.1; 530/351
[58] Field of Search ............................... 424/85.2, 85.1; 530/351

[56] References Cited

U.S. PATENT DOCUMENTS

| | | | |
|---|---|---|---|
| 4,690,915 | 9/1987 | Rosenberg | 530/351 |
| 4,877,561 | 10/1989 | Iga et al. | 264/4.3 |
| 4,962,091 | 10/1990 | Eppstein et al. | 424/85.2 |

FOREIGN PATENT DOCUMENTS

| | | | |
|---|---|---|---|
| 0405980 | 1/1991 | European Pat. Off. | C12N 15/24 |
| 9004633 | 5/1990 | WIPO | C12N 5/02 |
| 9010059 | 9/1990 | WIPO | C12N 5/08 |

OTHER PUBLICATIONS

Cross et al., Infection and Immunity, pp. 2741–2747 vol. 61 (7), Jul. 1993.
Jain, Scientific American, Jul. 1994, pp. 58–65.
Curti, Critical Reviews in Oncology/Hematology, vol. 14, pp. 29–39, 1993.
Natavson et al., Annals of Int. Medicine, vol. 129 (9), pp. 771–783, May 1994.
Konrad, Michael, "Biological Barriers to Protein Delivery," ed. Audus et al., Plenum Press, NY, Chap 14, 1993.
Wedner, Basic & Clinical Immunology, Chap 34, Appleton & Lange, 7th Edition, Eds Stites et al., 1991.
Osband et al., Immunology Today, vol. 11(6), pp. 193–195, 1990.
Mier et al., J. Clin. Immunol., vol. 8(6), pp. 426–436, 1988.
Martin et al., Cancer Rs., vol. 46, pp. 2189–2192, Apr. 1986.
Whicher et al. (1990) Clin. Chem. 36(7):1269–1281.
Rosenberg et al. (1986) Science 233:1318–1321.
Fiorentino et al. (1989, Dec.) J. Exp. Med. 170:2081–2095.
Ronald B. Herberman, "Multiple Functions of Natural Killer Cells, Including Immunoregulation as Well as Resistance to Tumor Growth," Concepts Immunopathol., 1:96–132, 1985.
Di-Hwei Hsu, et al., "Differential Effects of IL–4 and IL–10 on IL–2–induced IFN–γ Synthesis and Lymphokine–activated Killer Activity," Int. Immunol., 4:563–569, 1992.
Attan Kasid, et al., "Induction of Endogenous Cytokine–mRNA in Circulating Peripheral Blood Mononuclear Cells by IL–2 Administration to Cancer Patients," J. Immunol., 143:736–739, Jul. 1989.
Amy H. Kragel, et al., "Pathologic Findings Associated With Interleukin–2–Based Immunotherapy for Cancer: A Postmortem Study of 19 Patients," Human Pathology, 21:493–502, May 1990.
Ian A. MacNeil, et al., "IL–10, a Novel Growth Cofactor for Mature and Immature T Cells," J. Immunol., 145:4167–4173, Dec. 1990.
Steven A. Rosenberg, "Adoptive Immunotherapy for Cancer," Scientific American, pp. 62–68, May 1990.
Steven A. Rosenberg, et al., "Use of Tumor–Infiltrating Lymphocytes and Interleukin–2 in the Immunotherapy of Patients with Metastatic Melanoma," NE J. Med., 319:1676–1680, Dec. 1988.
Robert I. Tepper, et al., "Murine Interleukin–4 Displays Potent Anti–Tumor Activity In Vivo," Cell, 57:503–512, May 1989.
Suzanne L. Topalian, et al., "Expansion of Human Tumor Infiltrating Lymphocytes for Use in Immunotherapy Trials," J. Immunol. Methods, 102:127–141, 1987.

Primary Examiner—Chhaya D. Sayala
Attorney, Agent, or Firm—Cynthia L. Foulke; Norman C. Dulak; Edwin P. Ching

[57] ABSTRACT

A method is provided for using interleukin-10 in adoptive immunotherapy of cancer. A population of tumor-infiltrating lymphocytes (TILs) are expanded in culture in the presence of interleukin-2 (IL-2) and interleukin-10 (IL-10). After administration of the TILs to a patient, effective amounts of both IL-2 and IL-10 are administered to enhance the tumor cell cytotoxicity of the TILs and to reduce side effects caused by IL-2-induced cytokine production in the TILs and other cells of the patient.

20 Claims, 6 Drawing Sheets

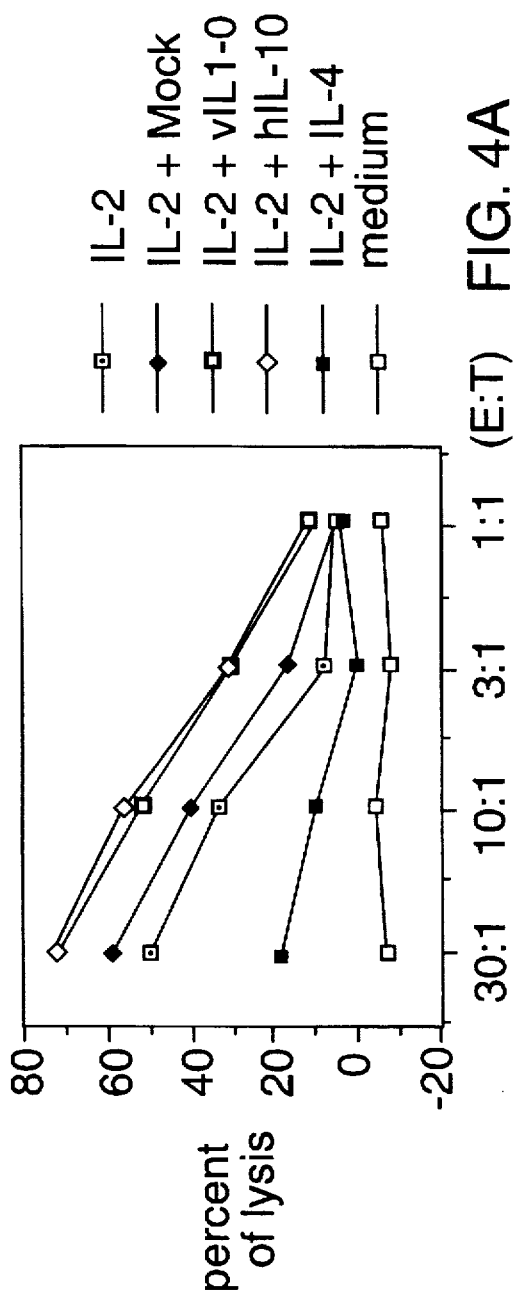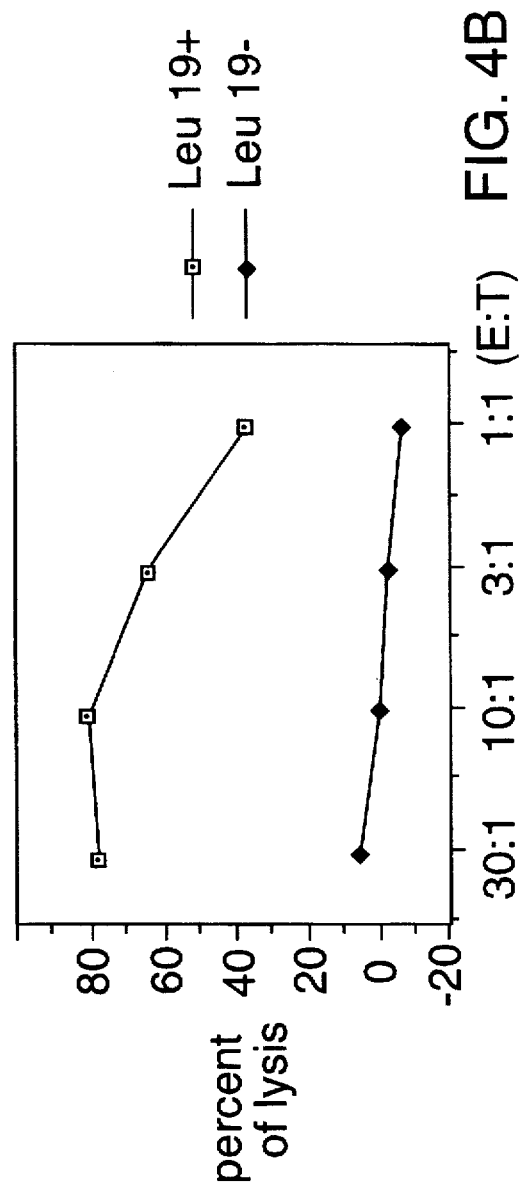

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 178 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met  His  Ser  Ser  Ala  Leu  Leu  Cys  Cys  Leu  Val  Leu  Leu  Thr  Gly  Val
1                        5                        10                       15

Arg  Ala  Ser  Pro  Gly  Gln  Gly  Thr  Gln  Ser  Glu  Asn  Ser  Cys  Thr  His
                    20                       25                       30

Phe  Pro  Gly  Asn  Leu  Pro  Asn  Met  Leu  Arg  Asp  Leu  Arg  Asp  Ala  Phe
               35                        40                       45

Ser  Arg  Val  Lys  Thr  Phe  Phe  Gln  Met  Lys  Asp  Gln  Leu  Asp  Asn  Leu
     50                        55                       60

Leu  Leu  Lys  Glu  Ser  Leu  Leu  Glu  Asp  Phe  Lys  Gly  Tyr  Leu  Gly  Cys
65                        70                       75                       80

Gln  Ala  Leu  Ser  Glu  Met  Ile  Gln  Phe  Tyr  Leu  Glu  Glu  Val  Met  Pro
                    85                       90                       95

Gln  Ala  Glu  Asn  Gln  Asp  Pro  Asp  Ile  Lys  Ala  His  Val  Asn  Ser  Leu
               100                      105                      110

Gly  Glu  Asn  Leu  Lys  Thr  Leu  Arg  Leu  Arg  Leu  Arg  Arg  Cys  His  Arg
          115                      120                      125

Phe  Leu  Pro  Cys  Glu  Asn  Lys  Ser  Lys  Ala  Val  Glu  Gln  Val  Lys  Asn
     130                      135                      140

Ala  Phe  Asn  Lys  Leu  Gln  Glu  Lys  Gly  Ile  Tyr  Lys  Ala  Met  Ser  Glu
145                      150                      155                      160

Phe  Asp  Ile  Phe  Ile  Asn  Tyr  Ile  Glu  Ala  Tyr  Met  Thr  Met  Lys  Ile
               165                      170                      175

Arg  Asn
```

( 2 ) INFORMATION FOR SEQ ID NO:2:

( i ) SEQUENCE CHARACTERISTICS:
        ( A ) LENGTH: 170 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Glu  Arg  Arg  Leu  Val  Val  Thr  Leu  Gln  Cys  Leu  Val  Leu  Leu  Tyr
1                        5                        10                       15

Leu  Ala  Pro  Glu  Cys  Gly  Gly  Thr  Asp  Gln  Cys  Asp  Asn  Phe  Pro  Gln
                    20                       25                       30
```

| | | | | | | | | | | | | | |
|---|---|---|---|---|---|---|---|---|---|---|---|---|---|
|Met|Leu|Arg 35|Asp|Leu|Arg|Asp 40|Ala|Phe|Ser|Arg|Val 45|Thr|Phe Phe|
|Gln|Thr 50|Lys|Asp|Glu|Val|Asp 55|Asn|Leu|Leu|Leu 60|Lys|Glu|Ser Leu Leu|
|Glu 65|Asp|Phe|Lys|Gly|Tyr 70|Leu|Gly|Cys|Gln|Ala 75|Leu|Ser|Glu Met Ile 80|
|Gln|Phe|Tyr|Leu|Glu 85|Glu|Val|Met|Pro|Gln 90|Ala|Glu|Asn|Gln Asp Pro 95|
|Glu|Ala|Lys|Asp 100|His|Val|Asn|Ser|Leu 105|Gly|Glu|Asn|Leu|Lys Thr Leu 110|
|Arg|Leu|Arg 115|Leu|Arg|Arg|Cys|His 120|Arg|Phe|Leu|Pro|Cys 125|Glu Asn Lys|
|Ser|Lys 130|Ala|Val|Glu|Gln|Ile 135|Lys|Asn|Ala|Phe|Asn 140|Lys|Leu Gln Glu|
|Lys 145|Gly|Ile|Tyr|Lys|Ala 150|Met|Ser|Glu|Phe|Asp 155|Ile|Phe|Ile Asn Tyr 160|
|Ile|Glu|Ala|Tyr|Met 165|Thr|Ile|Lys|Ala|Arg 170| | | | |

( 2 ) INFORMATION FOR SEQ ID NO:3:

( i ) SEQUENCE CHARACTERISTICS:
    ( A ) LENGTH: 160 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

| | | | | | | | | | | | | | |
|---|---|---|---|---|---|---|---|---|---|---|---|---|---|
|Ser 1|Pro|Gly|Gln|Gly 5|Thr|Gln|Ser|Glu|Asn 10|Ser|Cys|Thr|His Phe Pro 15|
|Gly|Asn|Leu|Pro 20|Asn|Met|Leu|Arg|Asp 25|Leu|Arg|Asp|Ala|Phe Ser Arg 30|
|Val|Lys|Thr 35|Phe|Phe|Gln|Met|Lys 40|Asp|Gln|Leu|Asp|Asn 45|Leu Leu Leu|
|Lys|Glu 50|Ser|Leu|Leu|Glu|Asp 55|Phe|Lys|Gly|Tyr|Leu 60|Gly|Cys Gln Ala|
|Leu 65|Ser|Glu|Met|Ile|Gln 70|Phe|Tyr|Leu|Glu|Glu 75|Val|Met|Pro Gln Ala 80|
|Glu|Asn|Gln|Asp|Pro 85|Asp|Ile|Lys|Ala|His 90|Val|Asn|Ser|Leu Gly Glu 95|
|Asn|Leu|Lys|Thr 100|Leu|Arg|Leu|Arg|Leu 105|Arg|Arg|Cys|His|Arg Phe Leu 110|
|Pro|Cys|Glu 115|Asn|Lys|Ser|Lys|Ala 120|Val|Glu|Gln|Val|Lys 125|Asn Ala Phe|
|Asn|Lys 130|Leu|Gln|Glu|Lys|Gly 135|Ile|Tyr|Lys|Ala|Met 140|Ser|Glu Phe Asp|
|Ile 145|Phe|Ile|Asn|Tyr|Ile 150|Glu|Ala|Tyr|Met|Thr 155|Met|Lys|Ile Arg Asn 160|

( 2 ) INFORMATION FOR SEQ ID NO:4:

( i ) SEQUENCE CHARACTERISTICS:
    ( A ) LENGTH: 147 amino acids
    ( B ) TYPE: amino acid
    ( C ) STRANDEDNESS: single
    ( D ) TOPOLOGY: linear (  i  i  ) MOLECULE TYPE: peptide ( x i ) SEQUENCE DESCRIPTION: SEQ ID NO:4:

```
Thr Asp Gln Cys Asp Asn Phe Pro Gln Met Leu Arg Asp Leu Arg Asp
1               5                   10                  15
Ala Phe Ser Arg Val Lys Thr Phe Gln Thr Lys Asp Glu Val Asp
            20              25                  30
Asn Leu Leu Leu Lys Glu Ser Leu Leu Glu Asp Phe Lys Gly Tyr Leu
        35                  40                  45
Gly Cys Gln Ala Leu Ser Glu Met Ile Gln Phe Tyr Leu Glu Glu Val
    50                  55                  60
Met Pro Gln Ala Glu Asn Gln Asp Pro Glu Ala Lys Asp His Val Asn
65                  70                  75                  80
Ser Leu Gly Glu Asn Leu Lys Thr Leu Arg Leu Arg Leu Arg Arg Cys
                85                  90                  95
His Arg Phe Leu Pro Cys Glu Asn Lys Ser Lys Ala Val Glu Gln Ile
            100                 105                 110
Lys Asn Ala Phe Asn Lys Leu Gln Glu Lys Gly Ile Tyr Lys Ala Met
            115                 120                 125
Ser Glu Phe Asp Ile Phe Ile Asn Tyr Ile Glu Ala Tyr Met Thr Ile
    130                 135                 140
Lys Ala Arg
145
```

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:5:

GTAAGGAGGT TTAAC                                                15

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:6:

ATGAGCTCAT                                                    10

( 2 ) INFORMATION FOR SEQ ID NO:7:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:7:

AGCCCAGGCC AGGGCACCCA GTCTGAGAAC AGCTGCACCC ACTTCCCAGG TAACCGGTAC    60

( 2 ) INFORMATION FOR SEQ ID NO:8:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:8:

```
CGGTTACCTG GGAAGTGGGT GCAGCTGTTC TCAGACTGGG TGCCCTGGCC TGGGCT        56
```

( 2 ) INFORMATION FOR SEQ ID NO:9:

( i ) SEQUENCE CHARACTERISTICS:
        ( A ) LENGTH: 62 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:9:

```
GTAACCTGCC TAACATGCTT CGAGATCTCC GAGATGCCTT CAGCAGAGTG AAGACTTTCT    60

TT                                                                    62
```

( 2 ) INFORMATION FOR SEQ ID NO:10:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:10:

```
CTTCACTCTG CTGAAGGCAT CTCGGAGATC TCGAAGCATG TTAGGCAG                  48
```

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:11:

```
CAAATGAAGG ATCAGCTGGA CAACTTGTTC TTAAG                                35
```

( 2 ) INFORMATION FOR SEQ ID NO:12:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:12:

```
CTTAAGAACA AGTTGTCCAG CTGATCCTTC ATTTGAAAGA AAGT                      44
```

( 2 ) INFORMATION FOR SEQ ID NO:13:

( i ) SEQUENCE CHARACTERISTICS:

( A ) LENGTH: 69 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:13:

GAGTCCTTGC TGGAGGACTT TAAGGGTTAC CTGGGTTGCC AAGCCTTGTC TGAGATGATC        60

CAGTTTTAT        69

( 2 ) INFORMATION FOR SEQ ID NO:14:

( i ) SEQUENCE CHARACTERISTICS:
( A ) LENGTH: 73 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:14:

CTAGATAAAA CTGGATCATC TCAGACAAGG CTTGGCAACC CAGGTAACCC TTAAAGTCCT        60

CCAGCAAGGA CTC        73

( 2 ) INFORMATION FOR SEQ ID NO:15:

( i ) SEQUENCE CHARACTERISTICS:
( A ) LENGTH: 61 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:15:

CTAGAGGAGG TGATGCCCCA AGCTGAGAAC CAAGACCCAG ACATCAAGGC GCATGTTAAC        60

G        61

( 2 ) INFORMATION FOR SEQ ID NO:16:

( i ) SEQUENCE CHARACTERISTICS:
( A ) LENGTH: 65 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:16:

TCGACGTTAA CATGCGCCTT GATGTCTGGG TCTTGGTTCT CAGCTTGGGG CATCACCTCC        60

TCTAG        65

( 2 ) INFORMATION FOR SEQ ID NO:17:

( i ) SEQUENCE CHARACTERISTICS:
( A ) LENGTH: 63 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:17:

AACTCCCTGG GGGAGAACCT GAAGACCCTC AGGCTGAGGC TACGGCGCTG TCATCGATCT        60

GCA        63

( 2 ) INFORMATION FOR SEQ ID NO:18:

( i ) SEQUENCE CHARACTERISTICS:
    ( A ) LENGTH: 59 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:18:

```
GATCGATGAC AGCGCCGTAG CCTCAGCCTG AGGGTCTTCA GGTTCTCCCC CAGGGAGTT         59
```

( 2 ) INFORMATION FOR SEQ ID NO:19:

( i ) SEQUENCE CHARACTERISTICS:
    ( A ) LENGTH: 60 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:19:

```
CGATTTCTTC CCTGTCAAAA CAAGAGCAAG GCCGTGGAGC AGGTGAAGAA CGCGTGCATG         60
```

( 2 ) INFORMATION FOR SEQ ID NO:20:

( i ) SEQUENCE CHARACTERISTICS:
    ( A ) LENGTH: 54 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:20:

```
CACGCGTTCT TCACCTGCTC CACGGCCTTG CTCTTGTTTT GACAGGGAAG AAAT              54
```

( 2 ) INFORMATION FOR SEQ ID NO:21:

( i ) SEQUENCE CHARACTERISTICS:
    ( A ) LENGTH: 58 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:21:

```
CGCGTTTAAT AATAAGCTCC AAGACAAAGG CATCTACAAA GCCATGAGTG AGTTTGAC          58
```

( 2 ) INFORMATION FOR SEQ ID NO:22:

( i ) SEQUENCE CHARACTERISTICS:
    ( A ) LENGTH: 45 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:22:

```
ACTCATGGCT TTGTAGATGC CTTTGTCTTG GAGCTTATTA TTAAA                        45
```

( 2 ) INFORMATION FOR SEQ ID NO:23:

( i ) SEQUENCE CHARACTERISTICS:

-continued ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:23:

| | | | | | |
|---|---|---|---|---|---|
| ATCTTCATCA | ACTACATAGA | AGCCTACATG | ACAATGAAGA | TACGAAACTG | A |

51

( 2 ) INFORMATION FOR SEQ ID NO:24:

( i ) SEQUENCE CHARACTERISTICS:
        ( A ) LENGTH: 64 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:24:

| | | | | | |
|---|---|---|---|---|---|
| AGCTTCAGTT | TCGTATCTTC | ATTGTCATGT | AGGCTTCTAT | GTAGTTGATG | AAGATGTCAA |

60

ACTC

64

( 2 ) INFORMATION FOR SEQ ID NO:25:

( i ) SEQUENCE CHARACTERISTICS:
        ( A ) LENGTH: 498 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:25:

| | | | | | |
|---|---|---|---|---|---|
| AATTCATGGA | GCGAAGGTTA | GTGGTCACTC | TGCAGTGCCT | GGTGCTGCTT | TACCTGGCAC |
| CTGAGTGTGG | AGGTACAGAC | CAATGTGACA | ATTTTCCCCA | GACCTAAGAG | ATGCCTTCAG |
| TCGTGTTAAA | ACCTTTTTCC | AGACAAAGGA | CGAGGTAGAT | AACCTTTTGC | TCAAGGAGTC |
| TCTGCTAGAG | GACTTTAAGG | ATGCCAGGCC | CTGTCAGAAA | TGATCCAATT | CTACCTGGAG |
| GAAGTCATGC | CACAGGCTGA | AACCAGGACC | CTGAAGCCAA | AGACCATGTC | AATTCTTTGG |
| GTGAAAATCT | AAAGACCCTA | CGGCTCCGCC | TGCGCAGGTG | CCACAGGTTC | CTGCCGTGTG |
| AGAACAAGAG | TAAAGCTGTG | GAACAGATAA | AAAATGCCTT | TAACAAGCTG | CAGGAAAAAG |
| GAATTTACAA | AGCCATGAGT | GAATTTGACA | TTTTTATTAA | CTACATAGAA | GCATACATGA |
| CAATTAAAGC | CAGGTGAG | | | | |

60

120

180

240

300

360

420

480

498

USE OF INTERLEUKIN-10 IN ADOPTIVE IMMUNOTHERAPY OF CANCER

This is a continuation of application Ser. No. 07/995,564, filed Dec. 23, 1992, now abandoned, which application is a continuation of application Ser. No. 07/830,493, filed Feb. 4, 1992, now abandoned, which application is a continuation of application Ser. No. 07/641,342, filed Jan. 16, 1991, now abandoned.

FIELD OF THE INVENTION

The invention relates generally to methods and compositions for treating neoplasms, or cancers, in humans, and more particularly, to the use of interleukin-10 (IL-10) compositions in adoptive immunotherapy of human cancers.

BACKGROUND

Immunologic approaches to cancer therapy are based on the notion that cancer cells have somehow evaded the body's defenses against aberrant or foreign cells and molecules, and that these defenses might be therapeutically stimulated to regain the lost ground, e.g. pgs. 623–648 in Klein, Immunology (Wiley-Interscience, New York, 1982). The recent observations that various immune effectors can directly or indirectly inhibit tumor growth has led to renewed interest in this approach to cancer therapy, e.g. Herberman, Concepts Immunopathol., Vol. 1, pgs. 96–132 (1985)(natural killer cells resist tumor cell growth); Rosenberg et al, Ann. Rev. Immunol., Vol. 4, pgs. 681–709 (1988)(clinical use of IL-2-activated killer cells to treat cancer); Ralph et al, J. Exp. Med., Vol. 167, pgs. 712–717 (1988)(tumoricidal activity by macrophages stimulated by lymphokines), Tepper et al, Cell, Vol. 57, pgs. 503–512 (1989)(IL-4 has anti-tumor activity), M. Cohen, "Lymphokines and Tumor Immunity," pgs. 237–253 in S. Cohen, ed. Lymphokines and the Immune Response (CRC Press, Boca Raton, 1990), and the like.

One immunologic approach that has shown clinical promise has been the so-called adoptive immunotherapy using interleukin-2 (IL-2)-activated killer cells; Rosenberg et al (cited above) and Rosenberg, Sci. Amer., pgs. 62–69 (May 1990). Unfortunately, the severe side effects caused directly or indirectly by IL-2 has been an obstacle to the development of routine treatment protocols based on the approach, e.g. Gaynor et al, Ann. Int. Med., Vol. 109, pgs. 953–958 (1988); Lee et al, J. Clin. Oncol., Vol. 7, pgs. 7–20 (1989); and Rosenberg et al, Human Path., Vol. 22, pgs. 493–502 (1990). It would be a major advance in this approach to cancer therapy if methods could be found to reduced the severity of side effects directly and indirectly caused by IL-2.

SUMMARY OF THE INVENTION

The invention relates to the use of interleukin-10 (IL-10) in adoptive immunotherapy of cancers. The invention also includes pharmaceutical compositions comprising interleukin-10 for use in adoptive immunotherapy. The invention is based in part on the discovery that IL-10 can prevent or reduce the production of cytokines believed to be responsible for many of the deleterious side effects currently encountered in adoptive immunotherapy. As used herein, the term "adoptive immunotherapy" means therapy involving the transfer of functional immune cells to a patient. Preferably, the cancer-fighting immune cells comprise tumor-infiltrating lymphocytes (TILs) originating from the patient him or herself. Broadly, the method of the invention comprises the steps of (i) culturing TILs in the presence of IL-2 and IL-10, (ii) administering the cultured TILs to the patient, and (iii) administering IL-2 and IL-10 to the patient after administration of the TILs.

Preferably, the interleukin-10 of the invention is selected from the group consisting of the mature polypeptides of the open reading frames defined by the following amino acid sequences:

Met His Ser Ser Ala Leu Leu Cys Cys Leu Val Leu Leu Thr Gly Val Arg Ala Ser Pro Gly Gln Gly Thr Gln Ser Glu Asn Ser Cys Thr His Phe Pro Gly Asn Leu Pro Asn Met Leu Arg Asp Leu Arg Asp Ala Phe Ser Arg Val Lys Thr Phe Phe Gln Met Lys Asp Gln Leu Asp Asn Leu Leu Leu Lys Glu Ser Leu Leu Glu Asp Phe Lys Gly Tyr Leu Gly Cys Gln Ala Leu Ser Glu Met Ile Gln Phe Tyr Leu Glu Glu Val Met Pro Gln Ala Glu Asn Gln Asp Pro Asp Ile Lys Ala His Val Asn Ser Leu Gly Glu Asn Leu Lys Thr Leu Arg Leu Arg Leu Arg Arg Cys His Arg Phe Leu Pro Cys Glu Asn Lys Ser Lys Ala Val Glu Gln Val Lys Asn Ala Phe Asn Lys Leu Gln Glu Lys Gly Ile Tyr Lys Ala Met Ser Glu Phe Asp Ile Phe Ile Asn Tyr Ile Glu Ala Tyr Met Thr Met Lys Ile Arg Asn (SEQ ID No: 1) and Met Glu Arg Arg Leu Val Val Thr Leu Gln Cys Leu Val Leu Leu Tyr Leu Ala Pro Glu Cys Gly Gly Thr Asp Gln Cys Asp Asn Phe Pro Gln Met Leu Arg Asp Leu Arg Asp Ala Phe Ser Arg Val Lys Thr Phe Phe Gln Thr Lys Asp Glu Val Asp Asn Leu Leu Leu Lys Glu Ser Leu Leu Glu Asp Phe Lys Gly Tyr Leu Gly Cys Gln Ala Leu Ser Glu Met Ile Gln Phe Tyr Leu Glu Glu Val Met Pro Gln Ala Glu Asn Gln Asp Pro Glu Ala Lys Asp His Val Asn Ser Leu Gly Glu Asn Leu Lys Thr Leu Arg Leu Arg Leu Arg Arg Cys His Arg Phe Leu Pro Cys Glu Asn Lys Ser Lys Ala Val Glu Gln Ile Lys Asn Ala Phe Asn Lys Leu Gln Glu Lys Gly Ile Tyr Lys Ala Met Ser Glu Phe Asp Ile Phe Ile Asn Tyr Ile Glu Ala Tyr Met Thr Ile Lys Ala Arg (SEQ. ID. No: 2), wherein the standard three letter abbreviation is used to indicate L-amino acids, starting from the N-terminus. These two forms of IL-10 are sometimes referred to as human IL-10 (or human cytokine synthesis inhibitory factor) and viral IL-10 (or BCRF1), respectively, e.g. Moore et al, Science, Vol. 248, pgs. 1230–1234 (1990); Vieira et al, Proc. Natl. Acad. Sci., Vol. 88, pgs. 1172–1176 (1991); Fiorentino et al, J. Exp. Med., Vol. 170, pgs. 2081–2095 (1989); Hsu et al, Science, Vol. 250, pgs. 830–832 (1990). More preferably, the mature IL-10 used in the method of the invention is selected from the group consisting of Ser Pro Gly Gln Gly Thr Gln Ser Glu Asn Ser Cys Thr His Phe Pro Gly Asn Leu Pro Asn Met Leu Arg Asp Leu Arg Asp Ala Phe Ser Arg Val Lys Thr Phe Phe Gln Met Lys Asp Gln Leu Asp Asn Leu Leu Leu Lys Glu Ser Leu Leu Glu Asp Phe Lys Gly Tyr Leu Gly Cys Gln Ala Leu Ser Glu Met Ile Gln Phe Tyr Leu Glu Glu Val Met Pro Gln Ala Glu Asn Gln Asp Pro Asp Ile Lys Ala His Val Asn Ser Leu Gly Glu Asn Leu Lys Thr Leu Arg Leu Arg Leu Arg Arg Cys His Arg Phe Leu Pro cys Glu Asn Lys Ser Lys Ala Val Glu Gln Val Lys Asn Ala Phe Asn Lys Leu Gln Glu Lys Gly Ile Tyr Lys Ala Met Ser Glu Phe Asp Ile Phe Ile Asn Tyr Ile Glu Ala Tyr Met Thr Met Lys Ile Arg Asn (SEQ. ID. NO: 3) and Thr Asp Gln Cys Asp Asn Phe Pro Gln Met Leu Arg Asp Leu Arg Asp Ala Phe Ser Arg Val Lys Thr Phe Phe Gln Thr Lys Asp Glu Val Asp Asn Leu Leu Leu Lys Glu Ser Leu Leu Glu Asp Phe Lys Gly Tyr Leu Gly Cys Gln Ala Leu Ser Glu Met Ile Gln Phe Tyr Leu Glu Glu Val Met Pro Gln Ala Glu Asn Gln Asp Pro Glu Ala Lys Asp His Val Asn Ser Leu Gly Glu Asn Leu Lys Thr Leu Arg Leu Arg Leu Arg Arg Cys His Arg Phe Leu Pro Cys Glu Asn Lys Ser Lys Ala Val Glu Gln Ile Lys Asn Ala Phe Asn Lys Leu Gln Glu Lys Gly Ile Tyr Lys Ala Met Ser Glu Phe Asp Ile Phe Ile Asn Tyr Ile Glu Ala Tyr Met Thr Ile Lys Ala Arg (SEQ ID No: 4).

BRIEF DESCRIPTION OF THE DRAWINGS

FIG. 4(a) illustrates data showing the affect of IL-4, vIL-10, and hIL-10 on the IL-2-induced cytotoxicity of PBMCs.

FIG. 4(b) illustrates data showing that CD56$^+$ (Leu 19$^+$) PBMCs express LAK activity in the presence of IL-10 and IL-2.

DETAILED DESCRIPTION OF THE INVENTION

Figure 1:
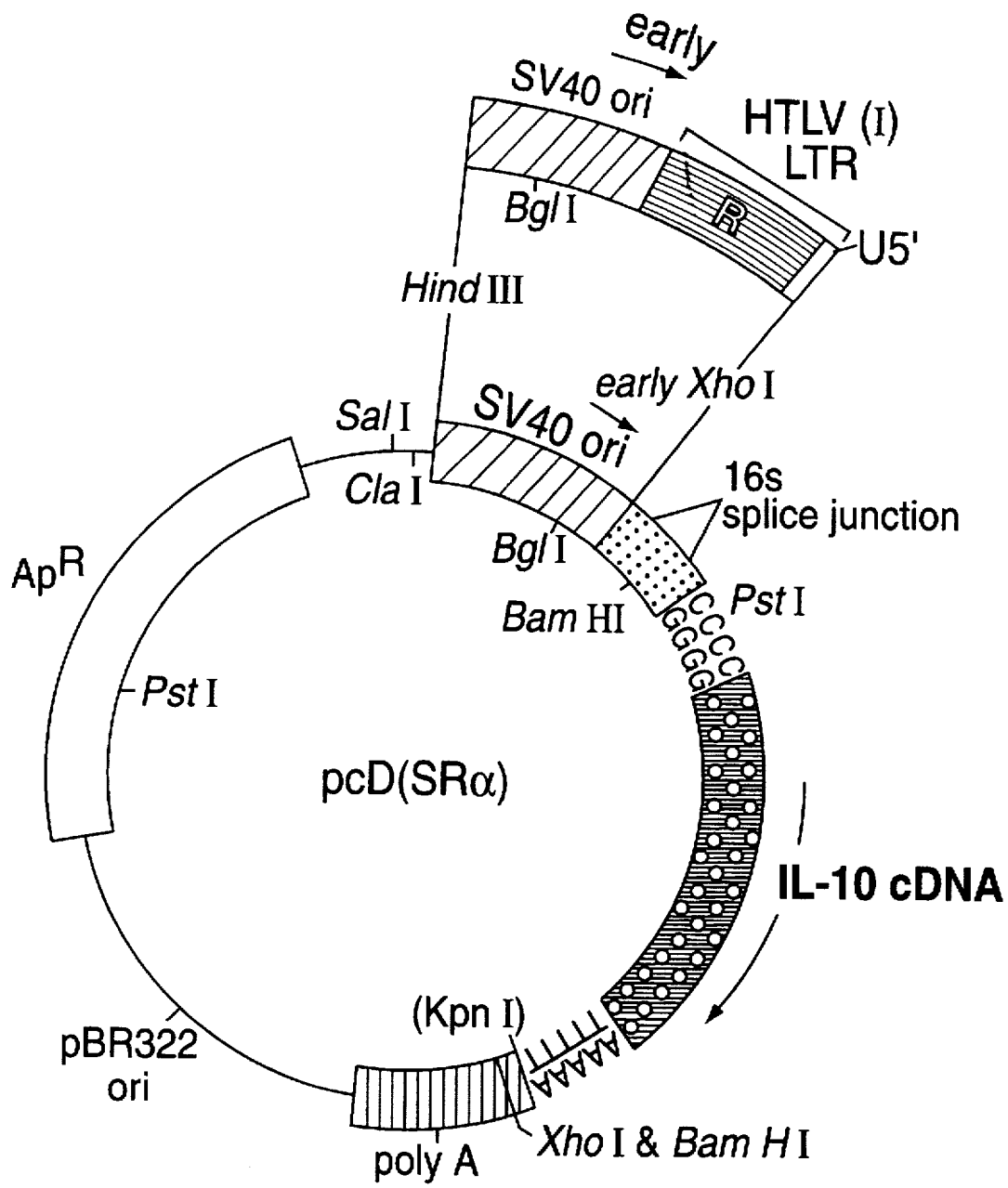
FIG. 1 is a diagrammatic representation of the mammalian expression vector pcD(SRα).

The invention is directed to a method of using IL-10 to reduce cytokine-induced side effects in adoptive immunotherapy of cancer. The invention also includes pharmaceutical compositions comprising IL-10 for carrying out the method. IL-10 for use in the invention is selected from the group of mature polypeptides encoded by the open reading frames defined by the cDNA inserts of pH5C, pH15C, and pBCRF1(SRa), which are deposited with the American Type Culture Collection (ATCC), Rockville, Md. under accession numbers 68191, 68192, and 68193, respectively.

Preferably, IL-10 is used in combination with IL-2 in adoptive immunotherapy as described by Rosenberg et al, Ann. Rev. Immunol., Vol. 4, pgs. 681–709 (1988); Topalian et al, J. Immunol. Meth., Vol. 102, pgs. 127–141 (1987); and Rosenberg et al, New Eng. J. Med., Vol. 319, pgs. 1676–1680 (1988). Accordingly, these references are incorporated by reference.

TILs are prepared as followed. Using sterile technique, solid tumors (preferably, 10–30 g) excised from a patient are dissected into 5 mm$^3$ pieces which are immersed in RPMI 1640 meduim containing hyaluronidase type V 0.01%, DNAse type I 0.002%, collagenase type IV 0.1% (e.g., Sigma, St. Louis, Mo.), penicillin 50 IU/ml, streptomycin 50 ug/ml (e.g. Flow Laboratories, McLean, Va.), and gentamicin 50 ug/ml (e.g., Gibco Laboratories, Chagrin Falls, Ohio). This mixture is stirred for 6–24 hours at room temperature, after which it is filtered through a coarse wire grid to exclude undigested tissue fragments. The resultant tumor cell suspension is centrifuged at 400 xg for 10 min. The pellet is washed twice with Hanks' balanced salt solution (HBSS) without Ca/Mg/phenol red (e.g., Whittaker MA Bioproducts, Walkersville, Md), then resuspended in HBSS and passed through Ficoll-Hypaque gradients (e.g. LSM, Bionetics, Kensington, Md). The gradient interfaces, containing viable tumor cells, lymphocytes, and monocytes are harvested and washed twice more with HBSS. The number of lymphocytes can be estimated visually, by cytologic examination, and/or by flow cytometry. The harvested cells may be frozen for storage in a type-compatible human serum containing 10% (v/v) DMSO.

At a concentration of about 2.5–5.0×10$^5$ viable cells/ml, single-cell tumor suspensions, obtained -either directly from the enzymatic digestion process described above or from rapid thawing of frozen specimens, are diluted in culture medium consisting of 20% (by volume) LAK cell supernatant (described below) and 80% (by volume) of RPMI 1640 medium containing 10% heat-inactivated human serum, penicillin, streptomycin, gentamicin, and amphotericin 250 ng/ml (Fungizone, Squibb, Flow Laboratories, McLean, Va.), Hepes buffer 10 mM, and L-glutamine 2 mM. IL-2 is added at a final concentration of 1000 U/ml (wherein units of IL-2 activity are defined as in Rosenberg et al, Science (cited above)) and IL-10 is added at a final concentration of between about 100–1000 U/ml (wherein units are defined below). TIL cultures are initiated by distributing the cells to 175 cm$^2$ flasks (e.g. Falcon, Becton Dickinson, Oxnard, Calif.), or the like, where they are maintained at 37° C. in a humidified 5% CO$_2$ atmosphere. TIL cultures are harvested, pelleted, and resuspended in fresh medium and fresh IL-2 on a weekly basis, or as dictated by the growth rate of the culture. TIL cultures are re-started at a concentration of about 2.5×10$^5$ viable cells/ml at each passage. After culturing for 9–28 days, and preferably for 30–40 days, tumor cells disappear from the cultures. TILs are harvested by centrifugation, resuspended in an isotonic saline solution, or like pharmiceutical carrier, and are infused into a patient (e.g. a maximum of 2×10$^{11}$ cells in 200–250 ml of carrier solution over a period of 30–60 minutes). Subsequent to the infusion of TILs, the patient is administered IL-2 and IL-10 as described below.

LAK cell supernatants are obtained as follows. Human peripheral blood lymphocytes, obtained either from leukapheresis specimens or from peripheral venous blood via standard Ficoll-Hypaque separation techniques, are suspended in RPMI 1640 medium with 2% heat-inactivated human AB serum, penicillin, streptomycin, and gentamicin at a cell concentration of about 1.0×10$^6$ cells/ml. IL-2 is added at a concentration of about 1000 U/ml, and the cells are incubated for 3–5 days. Culture supernatants are harvested by centrifugation and stored at 4° C. for use in the TIL cultures.

I. Expression of recombinant IL-10

A wide range of single-cell and multicellular expression systems (i.e. host-expression vector combinations) can be used to produce the polypeptides of the invention. Possible types of host cells include, but are not limited to, bacterial, yeast, insect, mammalian, and the like. Many reviews are available which provide guidance for making choices and/or modifications of specific expression systems e.g. to name a few, de Boer and Shepard, "Strategies for Optimizing Foreign Gene Expression in *Escherichia coli*," pgs. 205–247, in Kroon, ed. Genes: Structure and Expression (John Wiley & Sons, New York, 1983), review several *E. coli* expression systems; Kucherlapati et al., Critical Reviews in Biochemistry, Vol. 16, Issue 4, pgs. 349–379 (1984), and Banerji et al., Genetic Engineering, Vol. 5, pgs. 19–31 (1983) review methods for transfecting and transforming mammalian cells; Reznikoff and Gold, eds., Maximizing Gene Expression (Butterworths, Boston, 1986) review selected topics in gene expression in *E. coli*, yeast, and mammalian cells; and Thilly, Mammalian Cell Technology (Butterworths, Boston, 1986) reviews mammalian expression systems. Likewise, many reviews are available which describe techniques and conditions for, linking and/or manipulating specific cDNAs and expression control sequences to create and/or modify expression vectors suitable for use with the present invention, e.g. Sambrook et al (cited above).

An *E. coli* expression system is disclosed by Riggs in U.S. Pat. No. 4,431,739, which is incorporated by reference. A particularly useful prokaryotic promoter for high expression in *E. coli* is the tac promoter, disclosed by de Boer in U.S. Pat. No. 4,551,433, which is incorporated herein by reference. Secretion expression vectors are also available for *E. coli* hosts. Particularly useful are the pIN-III-ompA vectors, disclosed by Ghrayeb et al., in EMBO J., Vol. 3, pgs. 2437–2442 (1984), in which the cDNA to be transcribed is fused to the portion of the *E. coli* OmpA gene encoding the signal peptide of the ompA protein which, in turn, causes the mature protein to be secreted into the periplasmic space of the bacteria. U.S. Pat. Nos. 4,336,336 and 4,338,397 also disclose secretion expression vectors for prokaryotes. Accordingly, these references are incorporated by reference.

Numerous stains of bacteria are suitable hosts for prokaryotic expression vectors including strains of *E. coli*, such as W3110 (ATCC No. 27325), JA221, C600, ED767, DH1, LE392, HB101, X1776 (ATCC No. 31244), X2282, RR1 (ATCC No. 31343) MRCI; strains of *Bacillus subtilus;* and other enterobacteriaceae such as *Salmonella typhimurium* or *Serratia marcescens*, and various species of Pseudomonas. General methods for deriving bacterial strains, such as *E. coli* K12 X1776, useful in the expression of eukaryotic proteins is disclosed by Curtis III in U.S. Pat. No. 4,190,495. Accordingly this patent is incorporated by reference.

In addition to prokaryotic and eukaryotic microorganisms, expression systems comprising cells derived from multicellular organism may also be used to produce proteins of the invention. Of particular interest are mammalian expression systems because their posttranslational processing machinery is more likely to produce biologically active mammalian proteins. Several DNA tumor viruses have been used as vectors for mammalian hosts. Particularly important are the numerous vectors which comprise SV40 replication, transcription, and/or translation control sequences coupled to bacterial replication control sequences, e.g. the pcD vectors developed by Okayama and Berg, disclosed in Mol. Cell. Biol., Vol. 2, pgs. 161–170 (1982) and Mol. Cell. Biol., Vol. 3, pgs. 280–289 (1983), and improved by Takebe et al, Mol. Cell. Biol., Vol. 8, pgs. 466–472 (1988). Accordingly, these references are incorporated herein by reference. Other SV40-based mammalian expression vectors include those disclosed by Kaufman and Sharp, in Mol. Cell. Biol., Vol. 2, pgs. 1304–1319 (1982), and Clark et al., in U.S. Pat. No. 4,675,285, both of which are incorporated herein by reference. Monkey cells are usually the preferred hosts for the above vectors. Such vectors containing the SV40 ori sequences and an intact A gene can replicate autonomously in monkey cells (to give higher copy numbers and/or more stable copy numbers than nonautonomously replicating plasmids). Moreover, vectors containing the SV40 ori sequences without an intact A gene can replicate autonomously to high copy numbers (but not stably) in COS7 monkey cells, described by Gluzman, Cell, Vol. 23, pgs. 175–182 (1981) and available from the ATCC (accession no. CRL 1651). The above SV40-based vectors are also capable of transforming other mammalian cells, such as mouse L cells, by integration into the host cell DNA. Multicellular organisms can also serve as hosts for the production of the polypeptides of the invention, e.g. insect larvae, Maeda et al, Nature, Vol. 315, pgs. 592–594 (1985) and Ann. Rev. Entomol., pgs. 351–372 (1989); and transgenic animals, Jaenisch, Science, Vol. 240, pgs. 1468–1474 (1988).

II. Assays for Interleukin-10 and Definition of Units

IL-10s exhibit several biological activities which could form the basis of assays and units. In particular, IL-10s have property of inhibiting the synthesis of at least one cytokine in the group consisting of IFN-γ, lymphotoxin, IL-2, IL-3, and GM-CSF in a population of T helper cells induced to synthesize one or more of these cytokines by exposure to syngeneic antigen presenting cells (APCs) and antigen. In this activity, the APCs are treated so that they are incapable of replication, but that their antigen processing machinery remains functional. This is conveniently accomplished by irradiating the APCs, e.g. with about 1500–3000 R (gamma or X-radiation) before mixing with the T cells.

Alternatively, cytokine inhibition may be assayed in primary or, preferably, secondary mixed lymphocyte reactions (MLR), in which case syngeneic APCs need not be used. MLRs are well known in the art, e.g. Bradley, pgs. 162–166, in Mishell et al, eds. *Selected Methods in Cellular Immunology* (Freeman, San Francisco, 1980); and Battisto et al, Meth. in Enzymol., Vol. 150, pgs. 83–91 (1987). Briefly, two populations of allogenic lymphoid cells are mixed, one of the populations having been treated prior to mixing to prevent proliferation, e.g. by irradiation. Preferably, the cell populations are prepared at a concentration of about $2 \times 10^6$ cells/ml in supplemented medium, e.g. RPMI 1640 with 10% fetal calf serum. For both controls and test cultures, mix 0.5 ml of each population for the assay. For a secondary MLR, the cells remaining after 7 days in the primary MLR are restimulated by freshly prepared, irradiated stimulator cells. The sample suspected of containing IL-10 may be added to the test cultures at the time of mixing, and both controls and test cultures may be assayed for cytokine production from 1 to 3 days after mixing.

Obtaining T cell populations and/or APC populations for IL-10 assays employs techniques well known in the art which are fully described in DiSabato et al, eds., Meth. in Enzymol., Vol 108 (1984). APCs for the preferred IL-10 assay are peripheral blood monocytes. These are obtained using standard techniques, e.g. as described by Boyum, Meth. in Enzymol., Vol. 108, pgs. 88–102 (1984); Mage, Meth. in Enzymol., Vol. 108, pgs. 118–132 (1984); Litvin et al., Meth. in Enzymol., Vol. 108, pgs. 298–302 (1984); Stevenson, Meth. in Enzymol., Vol. 108, pgs. 242–249 (1989); and Romain et al, Meth. in Enzymol., Vol. 108, pgs. 148–153 (1984), which references are incorporated by reference. Preferably, helper T cells are used in the IL-10 assays, which are obtained by first separating lymphocytes from the peripheral blood then selecting, e.g. by panning or flow cytometry, helper cells using a commercially available anti-CD4 antibody, e.g. OKT4 described in U.S. Pat. No. 4,381,295 and available from Ortho Pharmaceutical Corp. The requisite techniques are fully disclosed in Boyum, Scand. J. Clin. Lab. Invest., Vol. 21 (Suppl. 97), pg. 77 (1968); Meth. in Enzymol., Vol. 108 (cited above), and in Bram et al, Meth. in Enzymol., Vol. 121, pgs. 737–748 (1986). Generally, PBLs are obtained from fresh blood by Ficoll-Hypaque density gradient centrifugation.

A variety of antigens can be employed in the assay, e.g. Keyhole limpet hemocyanin (KLH), fowl γ-globulin, or the like. More preferably, in place of antigen, helper T cells are stimulated with anti-CD3 monoclonal antibody, e.g. OKT3 disclosed in U.S. Pat. No. 4,361,549, in the assay.

Cytokine concentrations in control and test samples are measured by standard biological and/or immunochemical assays. Construction of immunochemical assays for specific cytokines is well known in the art when the purified cytokine is available, e.g. Campbell, *Monoclonal Antibody Technol-* ogy (Elsevier, Amsterdam, 1984); Tijssen, Practice and Theory of Enzyme Immunoassays (Elsevier, Amsterdam, 1985); and U.S. Pat. No. 4,486,530 are exemplary of the extensive literature on the subject. ELISA kits for human IL-2, human IL-3, and human GM-CSF are commercially available from Genzyme Corp. (Boston, Mass.); and an ELISA kit for human IFN-γ is commercially available from Endogen, Inc. (Boston, Mass.). Polyclonal antibodies specific for human lymphotoxin are available from Genzyme Corp. which can be used in a radioimmunoassay for human lymphotoxin, e.g. Chard, An Introduction to Radioimmunoassay and Related Techniques (Elsevier, Amsterdam, 1982).

Biological assays of the cytokines listed above can also be used to determine IL-10 activity. A biological assay for human lymphotoxin is disclosed in Aggarwal, Meth. in Enzymol., Vol. 116, pgs. 441–447 (1985), and Matthews et al, pgs. 221–225, in Clemens et al, eds., Lymphokines and Interferons: A Practical Approach (IRL Press, Washington, D.C., 1987). Human IL-2 and GM-CSF can be assayed with factor dependent cell lines CTLL-2 and KG-1, available from the ATCC under accession numbers TIB 214 and CCL 246, respectively. Human IL-3 can be assayed by it ability to stimulate the formation of a wide range of hematopoietic cell colonies in soft agar cultures, e.g. as described by Metcalf, The Hemopoietic Colony Stimulating Factors (Elsevier, Amsterdam, 1984). IFN-γ can be quantified with anti-viral assays, e.g. Meager, pgs. 129–147, in Clemens et al, eds. (cited above).

Cytokine production can also be determined by mRNA analysis. Cytokine mRNAs can be measured by cytoplasmic dot hybridization as described by White et al., J. Biol. Chem., Vol. 257, pgs. 8569–8572 (1982) and Gillespie et al., U.S. Pat. No. 4,483,920. Accordingly, these references are incorporated by reference. Other approaches include dot blotting using purified RNA, e.g. chapter 6, in Hames et al., eds., Nucleic Acid Hybridization A Practical Approach (IRL Press, Washington, D.C., 1985).

In some cases, samples to be tested for IL-10 activity must be pretreated to remove predetermined cytokines that might interfere with the assay. For example, IL-2 increases the production of IFN-γ in some cells. Thus depending on the helper T cells used in the assay, IL-2 may have to be removed from the sample being tested. Such removals are conveniently accomplished by passing the sample over a standard anti-cytokine affinity column.

For convenience, units of IL-10 activity are defined in terms of IL-10's ability to augment the IL-4-induced proliferation of MC/9 cells, which are described in U.S. pat. No. 4,559,310 and available from the ATCC under accession number CRL 8306. 1 unit/ml is defined as the concentration of IL-10 which gives 50% of maximum stimulation of MC/9 proliferation above the level of IL-4 in the following assay. Prepare duplicate or triplicate dilutions of IL-4 and IL-10 in 50 µl of medium per well in a standard microtiter plate. Medium consists of RPMI 1640, 10% fetal calf serum, 50 µM 2-mercaptoethanol, 2 mM glutamine, penicillin (100 U/L) and streptomycin (100 µg/L). Add IL-4, 25 µl/well of 1600 U/ml (400 U/ml final) diluted in medium and incubate overnight, e.g. 20–24 hours. $^3$H-thymidine (e.g. 50 µCi/ml in medium) is added at 0.5–1.0 µCi/well and the cells are again incubated overnight, after which cells are harvested and incorporated radioactivity measured.

III. Purificationt, Pharmaceutical Compositions, and Administration

When polypeptides of the present invention are expressed in soluble form, for example as a secreted product of transformed yeast or mammalian cells, they can be purified according to standard procedures of the art, including steps of ammonium sulfate precipitation, ion exchange chromatography, gel filtration, electrophoresis, affinity chromatography, and/or the like, e.g. "Enzyme Purification and Related Techniques," Methods in Enzymology, 22:233–577 (1977), and Scopes, R., Protein Purification: Principles and Practice (Springer-Verlag, New York, 1982) provide guidance in such purifications. Likewise, when polypeptides of the invention are expressed in insoluble form, for example as aggregates, inclusion bodies, or the like, they can be purified by standard procedures in the art, including separating the inclusion bodies from disrupted host cells by centrifugation, solublizing the inclusion bodies with chaotropic and reducing agents, diluting the solubilized mixture, and lowering the concentration of chaotropic agent and reducing agent so that the polypeptide takes on a biologically active conformation. The latter procedures are disclosed in the following references, which are incorporated by reference: Winkler et al, Biochemistry, 25: 4041–4045 (1986); Winkler et al, Biotechnology, 3: 992–998 (1985); Koths et al, U.S. Pat. No. 4,569,790; and European patent applications 86306917.5 and 86306353.3. Preferably, IL-10 of the invention is used in combination with human interleukin-2 (IL-2). IL-2 can be produced in accordance with Taniguchi et al, U.S. Pat. No. 4,738,927; Rosenberg et al, Science, Vol. 223, pgs. 1412–1415 (1984); Dorin et al, U.S. Pat. No. 4,748,234; Koth et al, U.S. pat. No. 4,569,790; and the like. Accordingly, these references are incorporated by reference.

Generally, IL-10 is administered as a pharmaceutical composition comprising a pharmaceutical carrier, an effective amount of IL-10, and IL-2. A pharmaceutical carrier can be any compatible, non-toxic substance suitable for delivering the compositions of the invention to a patient. Generally, compositions useful for parenteral administration of such drugs are well known, e.g. Remington's Pharmaceutical Science, 15th Ed. (Mack Publishing Company, Easton, Pa. 1980). Alternatively, compositions of the invention may be introduced into a patient's body by implantable or injectable drug delivery system, e.g. Urquhart et al., Ann. Rev. Pharmacol. Toxicol., Vol. 24, pgs. 199–236 (1984); Lewis, ed. Controlled Release of Pesticides and Pharmaceuticals (Plenum Press, New York, 1981); U.S. Pat. No. 3,773,919; U.S. Pat. No. 3,270,960; and the like.

When administered parenterally, the IL-10 is formulated in a unit dosage injectable form (solution, suspension, emulsion) in association with a pharmaceutical carrier. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other proteins at a concentration in the range of about 5 to 20 µg/ml.

As used herein "effective amount" of IL-10 means an amount sufficient to reduce or prevent side effects in adoptive immunotherapy. The effective amount for a particular patient may vary depending on such factors as the state and type of the neoplastic disease being treated, the overall health of the patient, method of administration, the severity of side effects, the amount and kinds of other drugs being used concurrently, and the like. Preferably, IL-10 is administered in the maximally tolerable dose. Likewise, IL-2 is also administered in the maximally tolerable dose (e.g. about 10⁵ U/kg, given intravenously every 8 hours in 50 ml of 0.9 percent saline with 5 percent albumin, or like carrier). Preferably, IL-2 and IL-10 are administered concurrently.

EXAMPLES

The following examples serve to illustrate the present invention. Selection of vectors and hosts as well as the concentration of reagents, temperatures, and the values of other variable parameters are only to exemplify application of the present invention and are not to be considered as limitations thereof.

EXAMPLE 1

Expression of human CSIF in a bacterial host

A synthetic human CSIF gene is assembled from a plurality of chemically synthesized double stranded DNA fragments to form an expression vector designated TAC-RBS-hCSIF. Cloning and expression are carried out in a standard bacterial system, for example *E. coli* K-12 strain JM101, JM103, or the like, described by Viera and Messing, in Gene, Vol. 19, pgs. 259–268 (1982). Restriction endonuclease digestions and ligase reactions are performed using standard protocols, e.g. Maniatis et al., Molecular Cloning: A Laboratory Manual (Cold Spring Harbor Laboratory, New York, 1982).

The alkaline method (Maniatis et al., cited above) is used for small scale plasmid preparations. For large scale preparations a modification of the alkaline method is used in which an equal volume of isopropanol is used to precipitate nucleic acids from the cleared lysate. Precipitation with cold 2.5M ammonium acetate is used to remove RNA prior to cesium chloride equilibrium density centrifugation and detection with ethidium bromide.

For filter hybridizations Whatman 540 filter circles are used to lift colonies which are then lysed and fixed by successive treatments with 0.5M NaOH, 1.5M NaCl; 1M Tris.HCl pH8.0, 1.5M NaCl (2 min each); and heating at 80° C. 25 (30 min). Hybridizations are in 6xSSPE, 20% formamide, 0.1% sodium dodecylsulphate (SDS), 100 mg/ml *E. coli* tRNA, 100 mg/ml Coomassie Brilliant Blue G-250 (Bio-Rad) at 42° C. for 6 hrs using ³²P-labelled (kinased) synthetic DNAs. (20xSSPE is prepared by dissolving 174 g of NaCl, 27.6 g of NaH₂PO₄9H2O, and 7.4 g of EDTA in 800 ml of H2O. pH is adjusted to 7.4 with NaOH, volume is adjusted to 1 liter, and sterilized by autoclaving). Filters are washed twice (15 min, room temperature) with 1xSSPE, 0.1% SDS. After autoradiography (Fuji RX film), positive colonies are located by aligning the regrown colonies with the blue-stained colonies on the filters. DNA is sequenced by the dideoxy method, Sanger et al. Proc. Natl. Acad. Sci., Vol. 74, pg. 5463 (1977). Templates for the dideoxy reactions are either single stranded DNAs of relevant regions recloned into M13mp vectors, e.g. Messing et al. Nucleic Acids Res., Vol. 9, pg. 309 (1981), or double-stranded DNA prepared by the minialkaline method and denatured with 0.2M NaOH (5 min, room temperature) and precipitated from 0.2M NaOH, 1.43M ammonium acetate by the addition of 2 volumes of ethanol. DNA is synthesized by phosphoramidite chemistry using Applied Biosystems 380A synthesizers. Synthesis, deprotection, cleavage and purification (7M urea PAGE, elution, DEAE-cellulose chromotography) are done as described in the 380A synthesizer manual.

Complementary strands of synthetic DNAs to be cloned (400 ng each) are mixed and phosphorylated with polynucleotide kinase in a reaction volume of 50 ml. This DNA is ligated with 1 mg of vector DNA digested with appropriate restriction enzymes, and ligations are in a volume of 50 ml at room temperature for 4 to 12 hours. Conditions for phosphorylation, restriction enzyme digestions, polymerase reactions, and ligation have been described (Maniatis et al., cited above). Colonies are scored for lacZ+ (when desired) by plating on L agar supplemented with ampicillin, isopropyl-1-thio-beta-D-galactoside (IPTG) (0.4 mM) and 5-bromo-4-chloro-3-indolyl-beta-D-galactopyranoside (x-gal) (40 mg/ml).

Figure 3:
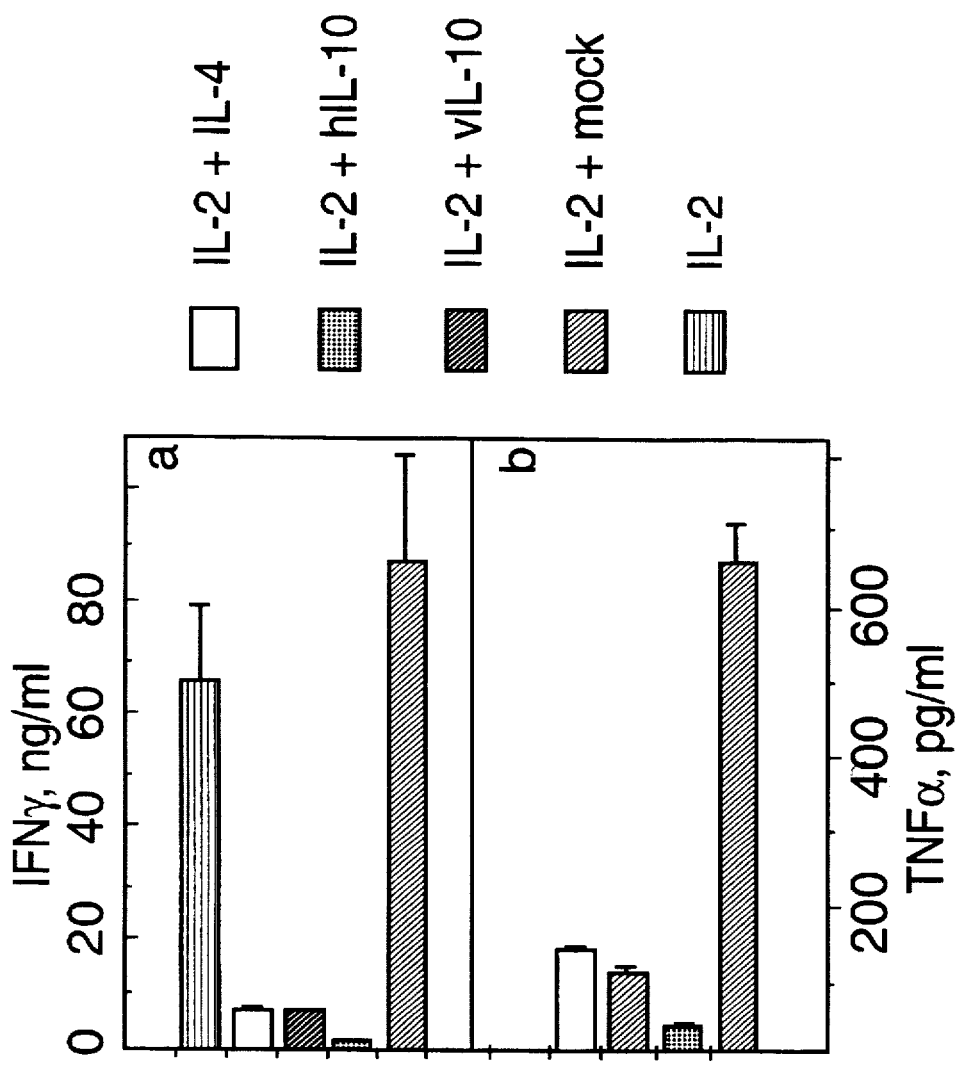
FIG. 3 illustrates data on cytokine synthesis of IL-2-activated PBMCs cultured in the presence of IL-2 and/or IL-4, vIL-10, and hIL-10.

The TAC-RBS vector is constructed by filling-in with DNA polymerase the single BamHI site of the tacP-bearing plasmid pDR540 (Pharmacia). This is then ligated to unphosphorylated synthetic oligonucleotides (Pharmacia) which form a double-stranded fragment encoding a consensus ribosome binding site (RBS, GTAAGGAGGTTTAAC) (SEQ. ID. No: 5). After ligation, the mixture is phosphorylated and religated with the SstI linker ATGAGCTCAT (SEQ. ID. No: 6). This complex was then cleaved with SstI and EcoRI, and the 173 bp fragment isolated via polyacrylamide gel electrophoresis (PAGE) and cloned into EcoRI-SstI restricted pUC19 (Pharmacia) (as described below). The sequence of the RBS-ATG-polylinker regions of the final construction (called TAC- RBS) is shown in FIG. 3.

The synthetic IL-10 gene is assembled into a pUC19 plasmid in eight steps. At each step inserts free of deletions and/or inserts can be detected after cloning by maintaining the lacZ(α) gene of pUC19 in frame with the ATG start codon inserted in step 1. Clones containing deletion and/or insertion changes can be filtered out by scoring for blue colonies on L-ampicillin plates containing x-gal and IPTG. Alternatively, at each step sequences of inserts can be readily confirmed using a universal sequencing primer on small scale plasmid DNA preparations, e.g. available from Boehringer Mannheim.

In step 1 the TAC-RBS vector is digested with SstI, treated with T4 DNA polymerase (whose 3' exonuclease activity digests the 3' protruding strands of the SstI cuts to form blunt end fragments), and after deactivation of T4 DNA polymerase, treated with EcoRI to form a 173 base pair (bp) fragment containing the TAC-RBS region and having a blunt end at the ATG start codon and the EcoRI cut at the opposite end. Finally, the 173 bp TAC-RBS fragment is isolated.

In step 2 the isolated TAC-RBS fragment of step 1 is mixed with EcoRI/KpnI digested plasmid pUC19 and synthetic fragment 1A/B which, as shown below, has a blunt end at its upstream terminus and a staggered end corresponding to an KpnI cut at its downstream terminus. This KpnI end is adjacent to and downstream of a BstEII site. The fragments are ligated to form the pUC19 of step 2.

In step 3 synthetic fragment 2A/B and 3A/B (shown below) are mixed with BstEII/SmaI digested pUC19 of step 2 (after amplification and purification) and ligated to form pUC19 of step 3. Note that the downstream terminus of fragment 3A/B contains extra bases which form the SmaI blunt end. These extra bases are cleaved in step 4. Also fragments 2A/B and 3A/B have complementary 9 residue single stranded ends which anneal upon mixture, leaving the upstream BstEII out of 2A/B and the downstream blunt end of 3A/B to ligate to the pUC19.

In step 4 AflII/XbaI digested pUC19 of step 3 (after amplification and purification) is repurified, mixed with synthetic fragment 4A/B (shown below), and ligated to form pUC19 of step 4.

In step 5 XbaI/SalI digested pUC19 of step 4 (after amplification and purification) is mixed with synthetic fragment 5A/B (shown below) and ligated to form the pUC19 of step 5. Note that the SalI staggered end of fragment 5A/B is eliminated by digestion with HpaI in step 6.

In step 6 HpaI/PstI digested pUC19 of step 5 (after amplification and purification) is mixed with synthetic fragment 6A/B (shown below) and ligated to form the pUC19 of step 6.

In step 7 ClaI/SphI digested pUC19 of step 6 (after amplification and purification) is mixed with synthetic fragment 7A/B (shown below) and ligated to form the pUC19 of step 7.

In step 8 MluI/HindIII digested pUC19 of step 7 (after amplification and purification) is mixed with synthetic fragments 8A/B and 9A/B and ligated to form the final construction. The final construction is inserted into $E.$ $coli$ K-12 strain JM101, e.g. available from the ATCC under accession number 33876, by standard techniques. After culturing, protein is extracted from the JM101 cells and dilutions of the extracts are tested for biological activity.

AGCCCAGGCC AGGGCACCCA GTCTGAGAAC AGCTGCACCC ACTTCTCGGGTCCGG TCCCGTGGGT CAGACTCTTG TCGACGTGGG TGAAGCCAGGtAACC ggtac (SEQ ID NO: 7)

GGTCCaTTGG c (SEQ ID NO: 8)

Fragment 1A/B

GtAACCTGCC TAACATGCTT CGAGATCTCC GAGATGCCTT CAGCAGACGG ATTGTACGAA GCTCTAGAGG CTCTACGGAA GTCGTGAGT-GAAGACTTTCTTT (SEQ ID NO: 9)

CTCACTTC (SEQ ID NO: 10)

Fragment 2A/B

CAAATGAAGG ATCAGCTGGA CAACTTGTTc TtAAG (SEQ ID NO: 11)

TGAAAGAAA GTTTACTTCC TAGTCGACCT GTTGAACAAg AaTTC (SEQ ID NO: 12)

Fragment 3A/B

GAGTCCTTGC TGGAGGACTT TAAGGGTTAC CTGGGTTGCC AAGCCCTCAGGAACG ACCTC-CTGAA ATTCCCAATG GACCCAACGG TTCGGT-TGTCTGAGA TGATCCAGTT TTAt (SEQ ID NO: 13)

AACAGACTCT ACTAGGTCAA AATaGAtC (SEQ ID NO: 14)

Fragment 4A/B

CTaGAGGAGG TGATGCCCCA AGCTGAGAAC CAAGACCCAG ACATCGAtCTCCTCC ACT-ACGGGGT TCGACTCTTG GTTCTGGGTC TGTA-GAAGGCGCATG TtAACg (SEQ ID NO:15)

TTCCGCGTAC AaTTGcagct (SEQ ID NO:16)

Fragment 5A/B

AACTCCCTGG GGGAGAACCT GAAGACCCTC AGGCTGAGGC TACGGTTGAGGGACC CCCTCT-TGGA CTTCTGGGAG TCCGACTCCG ATGC-CCGCTGTCATC GATctgca (SEQ ID NO: 17)

GCGACAGTAG CTAg (SEQ ID NO: 18)

Fragment 6A/B

CGATTTCTTC CCTGTCAAAA CAAGAGCAAG GCCGTGGAGC AGGTGTAAAGAAG GGA-CAGTTTT GTTCTCGTTC CGGCACCTCG TCCA-CAAGAAcGCgT gcatg (SEQ ID NO: 19)

TTCTTgCGcA c (SEQ ID NO: 20)

Fragment 7A/B

CGCGTTTAAT AATAAGCTCC AAGACAAAGG CATCTACAAA GCCATAAATTA TTATTCGAGG TTCT-GTTTCC GTAGATGTTT CGGTAGAGTGAGTTT GAC (SEQ ID NO: 21)

CTCA (SEQ ID NO: 22)

Fragment 8A/B

ATCTTCATCA ACTACATAGA AGCCTACATG ACAATCTCAAACTG TAGAAGTAGT TGATG-TATCT TCGGATGTAC TGTTAGAAGATACGA AACTGA (SEQ ID NO: 23)

CTTCTATGCT TTGACTtcga (SEQ ID NO: 24)

Fragment 9A/B (Lower case letters indicate that a base differs from that of the native sequence at the same site)

EXAMPLE 2

Expression of vIL-10 in COS 7 Monkey cells

A gene encoding the open reading frame for vIL-10 was amplified by polymerase chain reaction using primers that allowed later insertion of the amplified fragment into an Eco RI-digested pcD(SRα) vector (FIG. 1). The coding strand of the inserted fragment is shown below (the open reading frame being given in capital letters).

aattcATGGA GCGAAGGTTA GTGGTCACTC TGCAGTGCCT GGTGCTGCTT TACCTGGCAC CTGAGTGTGG AGGTACAGAC CAATGTGACA ATTTTCCCCA GACCTAAGAG ATGCCTTCAG TCGTGTTAAA ACCTTTTTCC AGACAAAGGA CGAGGTAGAT AACCTTTTGC TCAAGGAGTC TCTGCTAGAG GACTTTAAGG ATGCCAGGCC CTGTCAGAAA TGATCCAATT CTACCTGGAG GAAGTCATGC CACAGGCTGA AACCAGGAC CCTGAAGCCA AAGACCATGT CAATTCTTTG GGTGAAAATC TAAAGACCCT ACGGCTCCGC CTGCGCAGGT GCCACAGGTT CCTGCCGTGT GAGAACAAGA GTAAAGCTGT GGAACAGATA AAAAATGCCT TTAACAAGCT GCAGGAAAAA GGAATTTACA AAGCCATGAG TGAATTTGAC ATTTTTATTA ACTACATAGA AGCATACATG ACAATTAAAG CCAGGTGAg (SEQ ID NO: 25)

Clones carrying the insert in the proper orientation were identified by expression of vIL-10 and/or the electrophoretic pattern of restriction digests. One such vector carrying the vIL-10 gene was designated pBCRF1(SRα) and was deposited with the ATCC under accession number 68193. pBCRF1(SRα) was amplified in $E.$ $coli$ MC1061, isolated by standard techniques, and used to transfect COS 7 monkey cells as follows: One day prior to transfection, approximately 1.5×10⁶ COS 7 monkey cells were seeded onto individual 100 mm plates in Dulbecco's modified Eagle medium (DME) containing 5% fetal calf serum (FCS) and 2 mM glutamine. To perform the transfection, COS 7 cells were removed from the dishes by incubation with trypsin, washed twice in serum-free DME, and suspended to 10⁷ cells/ml in serum-free DME. A 0.75 ml aliquot was mixed with 20 μg DNA and transferred to a sterile 0.4 cm electroporation cuvette. After 10 minutes, the cells were pulsed at 200 volts, 960 μF in a BioRad Gene Pulser unit. After another 10 minutes, the cells were removed from the cuvette and added to 20 ml of DME containing 5% FCS, 2 mM glutamine, penicillin, streptomycin, and gentamycin. The mixture was aliquoted to four 100 mm tissue culture dishes. After 12–24 hours at 37° C., 5% $CO_2$, the medium was replaced with similar medium containing only 1% FCS and the incubation continued for an additional 72 hours at 37° C., 5% $CO_2$, after which the medium was collected and assayed for its ability to inhibit IFN-γ synthesis.

10 ml aliquots of freshly isolated PBLs (about $2\times10^6$ cells/ml) were incubated at 37° C. with PHA (100 ng/ml) in medium consisting of (i) 90% DME supplemented with 5% FCS and 2 mM glutamine, and (ii) 10% supernatant from COS 7 cells previously transfected with pBCRF1(SRα). After 24 hours the cells and supernatants were harvested to assay for the presence of either IFN-γ mRNA or IFN-γ protein, respectively. Controls were treated identically, except that the 10% supernatant was from COS 7 cultures previously transfected with a plasmid carrying an unrelated cDNA insert. The vIL-10-treated samples exhibited about a 50% inhibition of IFN-γ synthesis relative to the controls.

EXAMPLE 2

Expression of vIL-10 in *Escherichia coli*

A gene encoding the following mature vIL-10 may be expressed in *E. coli*.

Thr Asp Gln Cys Asp Asn Phe Pro Gln Met Leu Arg Asp
Leu Arg Asp Ala Phe Ser Arg Val Lys Thr Phe Phe Gln
Thr Lys Asp Glu Val Asp Asn Leu Leu Leu Lys Glu Ser
Leu Leu Glu Asp Phe Lys Gly Tyr Leu Gly Cys Gln Ala
Leu Ser Glu Met Ile Gln Phe Tyr Leu Glu Glu Val Met
Pro Gln Ala Glu Asn Gln Asp Pro Glu Ala Lys Asp His
Val Asn Ser Leu Gly Glu Asn Leu Lys Thr Leu Arg Leu
Arg Leu Arg Arg Cys His Arg Phe Leu Pro Cys Glu Asn
Lys Ser Lys Ala Val Glu Gln Ile Lys Asn Ala Phe Asn
Lys Leu Gln Glu Lys Gly Ile Tyr Lys Ala Met Ser Glu
Phe Asp Ile Phe Ile Asn Tyr Ile Glu Ala Tyr Met Thr Ile
Lys Ala Arg. (SEQ ID NO: 4)

The cDNA insert of pBCRF1(SRα) is recloned into an M13 plasmid where it is altered twice by site-directed mutagenesis: first to form a Cla I site at the 5' end of the coding region for the mature vIL-10 polypeptide, and second to form a Bam HI site at the 3' end of the coding region for the mature vIL-10 polypeptide. The mutated sequence is then readily inserted into the TRPC11 expression vector described below.

Figure 2:
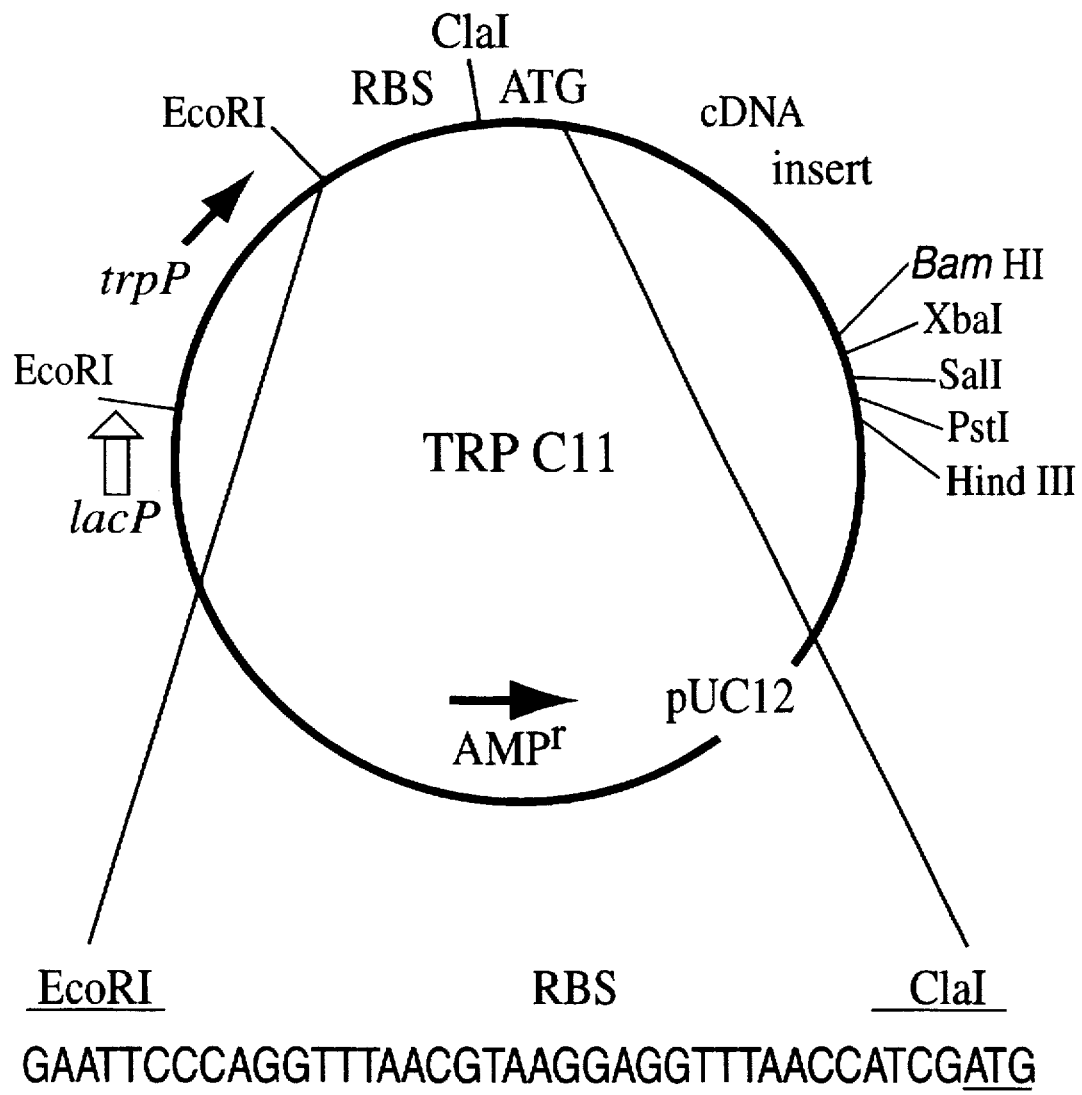
FIG. 2 is a diagrammatic representation of the bacterial expression vector TRP-C11.

The TRPC11 vector was constructed by ligating a synthetic consensus RBS fragment to ClaI linkers (ATGCAT) and by cloning the resulting fragments into ClaI restricted pMT11hc (which had been previously modified to contain the ClaI site). pMT11hc is a small (2.3 kilobase) high copy, $AMP^R$, $TET^S$ derivative of pBR322 that bears the πVX plasmid EcoRI-HindIII polylinker region. (πVX is described by Maniatis et al., Molecular Cloning: A Laboratory Manual, Cold Spring Harbor Laboratory, 1982). This was modified to contain the ClaI site by restricting pMT11hc with EcoRI and BamHI, filling in the resulting sticky ends and ligating with ClaI linker (CATCGATG), thereby restoring the EcoRI and BamHI sites and replacing the SmaI site with a ClaI site. One transformant from the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI, and treating with T4 DNA polymerase in the presence of all four deoxynucleotide triphosphates. The resulting 30–40 bp fragments were recovered via PAGE and cloned into SmaI restricted pUC12. A 248 bp *E. coli* trpP-bearing EcoRI fragment derived from pKC101 (described by Nichols, et al. in Methods in Enzymology, Vol. 101, pg. 155 (Academic Press, N.Y. 1983)) was then cloned into the EcoRI site to complete the TRPC11 construction, which is illustrated in FIG. 2. TRPC11 is employed as a vector for vIL-10 by first digesting it with ClaI and Bam HI, purifying it, and then mixing it in a standard ligation solution with the ClaI-Bam HI fragment of the M13 containing the nucleotide sequence coding for the mature BCRF1. The insert-containing TRPC11, referred to as TRPC11-BCRF1, is propagated in *E. coli* K12 strain JM101, e.g. available from the ATCC under accession number 33876.

EXAMPLE 4

Differential Effects of IL-4 and IL-10 on IL-2-induced interferon-γ Synthesis and Cytotoxicity in human NK cells It is shown that IL-4, hIL-10, and vIL-10 inhibit synthesis of interferon-γ (INFγ) and tumor necrosis factor-α (TNFα) by IL-2-stimulated peripheral blood mononuclear cells (PBMC), but only IL-4 inhibits INFγ synthesis by purified NK cells. Addition of monocytes, but not T cells, as accessory cells restored the inhibitory effect of hIL-10/vIL-10 on INFγ synthesis by NK cells. Unlike IL-4, hIL-10 and vIL-10 do not inhibit induction of lymphokine-activated killer (LAK) activity in PBMC by IL-2, which is predominantly mediated by NK cells. Thus IL-4 and IL-10 act on NK cells via distinct mechanisms.

Recombinant hIL-10, vIL-10, and hIL-4 were, tested for their effects on synthesis of INFγ and TNFα, and LAK activity induced by IL-2 in peripheral blood mononuclear cells (PBMC). $10^6$ cells were cultured in 200 u/ml of rIL-2 with either IL-4 (200 unit/ml) or COS7 supernatants containing hIL-10, vIL-10, or no cytokine (mock) for 5 days, after which cytokine synthesis was measured. LAK activity was assessed against the Burkitt lymphoma cell line Daudi, which is killed efficiently by LAK cells, but not by fresh NK cells. IL-2-induced INFγ and TNFα synthesis in cultures containing hIL-10, vIL-10, or IL-4 was substantially inhibited (FIG. 3). In contrast, IL-2-induced LAK activity against Daudi cells was inhibited only in cultures containing IL-4, and was unchanged or even slightly enhanced in the hIL-10 and vIL-10 cultures (FIG. 4a). IL-2-induced LAK activity is mediated primarily by CD56(Leu19)+NK cells. Phillips et al. J. Exp. Med., Vol. 164, pgs. 814–825 (1986); and Ortaldo et al. J. Exp. Med., vol. 164, pgs. 1193–1205 (1986). To determine the phenotype of LAK cells induced in PBMC cultured with IL-2 and hIL-10 or vIL-10, CD56-positive and -negative populations were sorted by FACS and tested for cytotoxicity against Daudi cells. FIG. 4b shows that, as with IL-2 alone, significant LAK activity was observed only in the CD56+ population. Thus, while IL-4 and IL-10 both inhibit IL-2-induced synthesis of IFNg and TNFa, only IL-4 inhibits IL-2-induced cytotoxicity in PBMC.

Figure 5A:
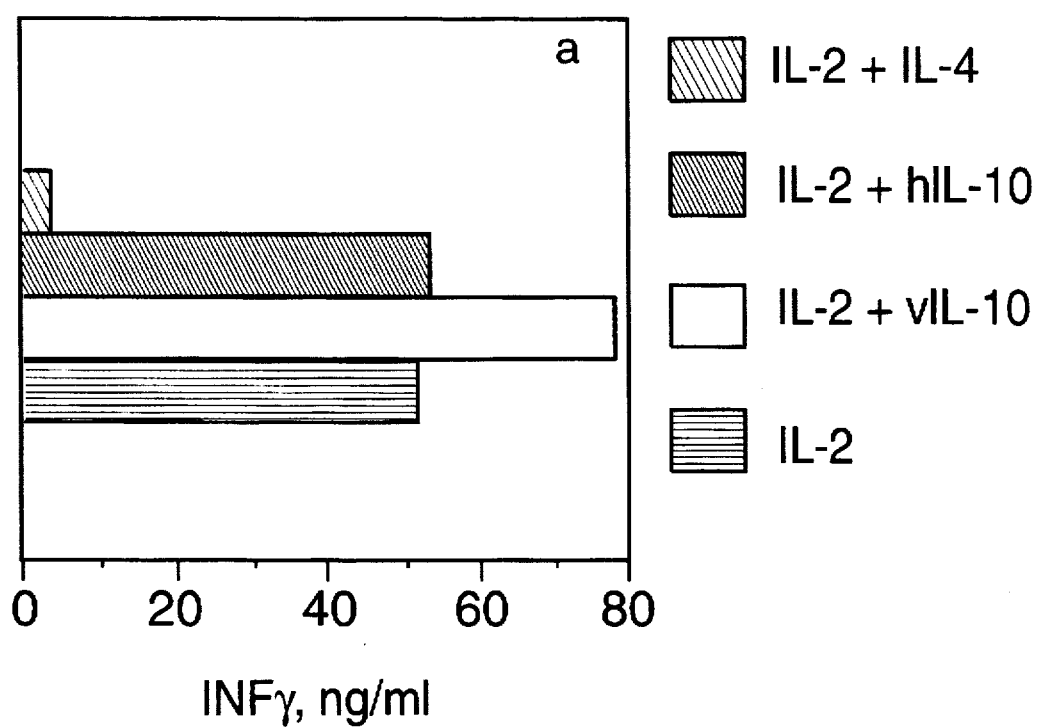
FIG. 5(a) illustrates data showing the affect of IL-4, vIL-10, and hIL-10 on IFNγ production in purified NK cells.

The majority of IL-2-induced IFNγ synthesis in PBMC is derived from NK cells rather than T cells, e.g. Trinchieri et al. J. Exp. Med., Vol. 160, pgs. 1147–1169 (1984). Therefore the effect of hIL-10, vIL-10, and IL-4 on IL-2-induced IFNγ synthesis was tested by FACS-purified NK cells (purity >99.5%). IL-4 inhibited IL-2-induced IFNγ secretion by these cells; in contrast, neither hIL-10 nor vIL-10 suppressed IFNγ synthesis by purified fresh NK cells (FIG. 5a).

Figure 5B:
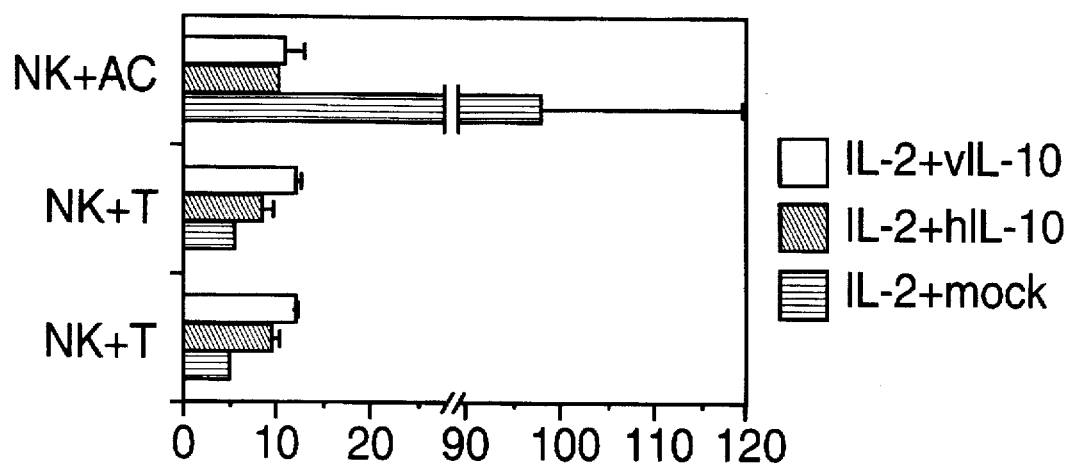
FIGS. 5(b) and (c) illustrate data showing the affect of monocytes on IFNγ production by purified NK cells cultured in the presence of IL-2 and/or hIL-10 and vIL-10.

That IFNγ synthesis was inhibited by IL-10 in cultures of PMBC but not pure NK cells suggested that this effect of IL-10 was mediated by an accessory cell population. NK cells were purified by sorting CD56+ cells from the low-density cell fraction obtained by percoll gradient centrifugation, and were mixed with plastic-adherent cells or with the high-density cell population (98% T cells). Addition of adherent cells to the NK cells strongly enhanced IL-2-induced IFNγ production by NK cells. This stimulatory effect of adherent cells was blocked by IL-10 (FIG. 5b). The T cell-containing fraction had no effect on IL-2-induced IFNg production by NK cells and did not mediate inhibition of IFNγ production by IL-10 (FIG 5b). Although most plastic-adherent cells are monocytes, it was confirmed that monocytes both enhance IL-2-induced IFNγ production and mediate its inhibition by IL-10: NK cells and CD14+ monocytes were purified by sorting and cultured in the presence of IL-2 and IL-10. FIG. 3c shows that addition of purified monocytes to NK cells enhanced IL-2-induced INFγ production. Moreover, IL-10 inhibited IL-2-induced INFγ production only in the presence of monocytes.

These results show that IL-4 and h.vIL-10 suppressed IFNγ and TNFα synthesis by IL-2-stimulated PBMC, but only IL-4 inhibited IL-2-induced LAK activity. These observations indicate that IL-2-induced cytokine production and cytotoxicity by NK cells are regulated via different pathways. Furthermore, the inhibitory effect of IL-10 on IFNγ synthesis by NK cells is indirect and mediated by monocytes, while IL-4 acts on NK cells in the absence of accessory cells.

IL-4, hIL-10 and vIL-10 inhibit IFNg synthesis by IL-2-activated PBMC (FIG. 3). Human PBMC were isolated from buffy coats from healthy donors by centrifugation over Ficoll-Hypaque and cultured at 10⁶/ml. in rIL-2 (200 unit/ml), with either rIL-4 (200 unit/ml), 10% COS-hIL-10, 10% COS-vIL-10 or 10% COS-mock in Yssel's medium with 1% human AB+ serum, Yssel et al, Immunol. Meth., Vol. 72, pgs. 219–227 (1984). Cultures were carried out in 24-well plates and supernatants were harvested for measuring INFγ by ELISA, e.g. as described by Hsu et al, Science, Vol. 250, pgs. 830–832 (1990). TNFa was also measured by ELISA (Endogen, Boston, Mass.). Cytokine production in the absence of IL-2 was below the limits of sensitivity of the INFγ and TNFα ELISAs, which were 0.3 ng/ml and 10 pg/ml, respectively. Error bars show the range of duplicate samples. PBMC from different donors varied in their capacity to produce IFNγ and TNFα when stimulated by IL-2; however, these experiments have been repeated more than a dozen times (IFNγ) and three times (TNFα) with qualitatively similar results.

IL-4, but, not hIL-10 or vIL-10, inhibits cytotoxicity induced by IL-2 in PBMC (FIG. 4a). PBMC from an experiment similar to that of FIG. 1 were harvested along with the supernatants and tested for cytotoxicity against ⁵¹Cr-labelled Daudi cells. LAK activity is expressed by CD56+ cells in PBMC cultured with IL-2 and IL-10 (FIG. 4b). PBMC were stained with anti-CD56 antibody conjugated to FITC, and sorted on a FacStar Plus (Becton-Dickinson, San Jose, Calif.). Cytotoxic activity in the CD56+ and CD56- (purity 99.7%) fractions was tested as described in Spits et al, J. Immunol., Vol. 141, pgs. 29–36 (1988).

Figure 5C:
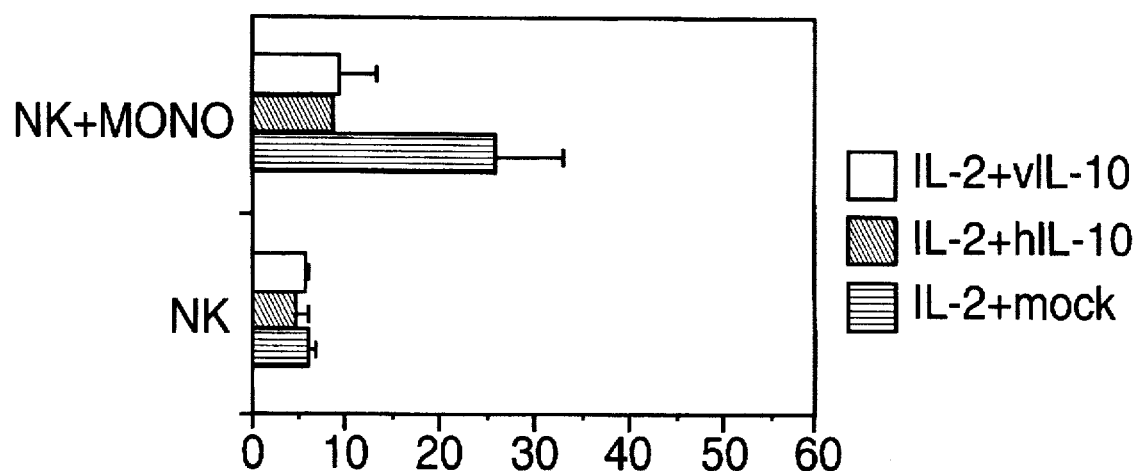

IL-2-induced INFγ synthesis by purified NK cells is directly inhibited by IL-4 but not by h.vIL-10 (FIG. 5a). FACS-purified NK cells (purity>99.5%) were cultured at 10⁶ cells/ml with 200 unit/ml rIL-2 with either 500 unit/ml rIL4, or COS-hIL-10, COS-vIL-10, or COS-mock supernatants (10%) in Yssel's medium for 4–5 days, then supernatants from duplicate cultures were collected and mixed for measurement of IFNγ by ELISA. Addition of adherent cells, but not T cells, restored IL-10-mediated inhibition of IL-2-induced INFγ synthesis by purified NK cells (FIG. 5b). Addition of purified monocytes restored IL-10-mediated inhibition of IL-2-induced IFNγ synthesis by purified NK cells. Monocytes alone did not produce IFNγ. (FIG.5c) PBMC were washed and incubated in tissue culture dishes for 40 min, 37° C. Adherent cells were collected by scraping with a rubber policeman. Non-adherent cells were removed, pelleted, and applied to a nylon wool column and incubated for 40 min at 37°. After elution from the column, cells were pelleted and resuspended in 30% Percoll with 10% FCS/PBS and layered on 40% Percoll. Following centrifugation for 30 min at room temperature, the large granular lymphocytes at the interface were recovered and washed twice. These cells were incubated with anti-CD56 antibody (Becton-Dickinson, San Jose, Calif.) for 30 min at 4°, washed, and then stained with goat-anti-mouse-FITC (Jackson Immunoresearch, Avondale, Pa.) prior to FACS sorting. CD56+ cells comprised about 35–50% of the cells subjected to sorting. Sorted cells were greater than 99.5% CD56+ upon reanalysis. Purified NK cells (9×10⁵ cells/ml) were mixed with adherent cells or T cells (3×10⁵) in a final volume of 100 ml and cultured with IL-2+hIL-10, vIL-10, or mock supernatant as described above. Supernatants were harvested and tested for IFNγ production. Error bars show the range of duplicate samples. NK cells and monocytes from the same donor were obtained as follows: PBMC were incubated with sheep blood red cells overnight; rosetting (CD2+) and non-rosettig cells were separated by centrifugation over a ficoll-hypaque gradient. E+ cells were subjected to the same purification procedure as described for PBMC (see above) to obtain purified NK cells. E-cells were incubated subsequently with anti-CD14 mAb (LeuM3) and FITC-labelled goat anti-mouse IgG antibody and the CD14+ cells were sorted with the FACStar plus. Purity of these cells was greater than 98%. Purified NK cells (10⁶ cells/ml) were mixed with pure monocytes (10⁵ cells/ml) in 100 ml and cultured alone or with IL-2+hIL-10, vIL-10, or mock supernatant as described above. Supernatants were harvested and tested for IFNγ production. IFNγ production in the absence of IL-2 was below the limits of detection. Error bars show the range of duplicate samples. NK cells from different donors varied in their capacity to produce IFNγ.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

Applicants have deposited separate cultures of *E. coli* MC1061 carrying pH5C, pH15C, and pBCRF1(SRα) with the American Type Culture Collection, Rockville, Md, USA (ATCC), under accession numbers 68191, 68192, and 68193, respectively. These deposits were made under conditions as provided under ATCC's agreement for Culture Deposit for Patent Purposes, which assures that the deposit will be made available to the U.S. Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

---

We claim:

1. A method of treating an individual for cancer, comprising:
    (a) culturing tumor-infiltrating lymphocytes in the presence of interleukin-2 and interleukin-10 so that the tumor-infiltrating lymphocytes proliferate;
    (b) administering the cultured tumor-infiltrating lymphocytes to a individual afflicted with cancer; and
    (c) administering an effective amount of interleukin-2 and interleukin-10 to the individual after administration of the cultured tumor-infiltrating lymphocytes.

2. The method of claim 1 in which the tumor-infiltrating lymphocytes are from a tumor excised from said individual.

3. The method of claim 2 in which from about $1 \times 10^{10}$ to about $2 \times 10^{11}$ of said cultured tumor-infiltrating lymphocytes are administered by intravenous infusion.

4. A method of treating an individual for cancer, comprising:
    (a) culturing peripheral blood cells in the presence of interleukin-2 and interleukin-10 to induce production of LAK cells;
    (b) administering the LAK cells to an individual afflicted with cancer; and
    (c) administering an effective amount of interleukin-2 and interleukin-10 to the individual after administration of the LAK cells.

5. A pharmaceutical composition comprising the combination of interleukin-2 and interleukin-10, and a physiologically acceptable carrier.

6. The method of claim 1 in which the administering of interleukin-2 and interleukin-10 is concurrent.

7. The method of claim 1, wherein said interleukin-2 is human interleukin-2.

8. The method of claim 1, wherein said interleukin-10 is human or viral interleukin-10.

9. The method of claim 1, wherein said interleukin-2 and/or said interleukin-10 is administered parenterally.

10. The method of claim 1, wherein said administering of cultured tumor-infiltrating lymphocytes and sid administering of interleukin-2 and interleukin-10 are concurrent.

11. the meod of claim 1, wherein said culturing is for at least 9 days, wherein tumor cells are depleted from said culture.

12. The method of claim 4 in which the peripheral blood cells are from said individual.

13. The method of claim 4, wherein said interleukin-2 is human interleukin-2.

14. The method of claim 4, wherein said interleukin-10 is human or viral interleukin-10.

15. The method of claim 4, wherein said interleukin-2 and/or said interleukin-10 is administered parenterally.

16. The pharmaceutical composition of claim 5, wherein said interleukin-2 is human interleukin-2.

17. The pharmaceutical composition of claim 5, wherein said interleukin-10 is human or viral interleukin-10.

18. The pharmaceutical composition of claim 5 in a single dose form for administration to TIL or LAK cells.

19. The pharmaceutical composition of claim 5 in a single dose form for administration to an individual.

20. The pharmaceutical composition of claim 5, in an implantable or injectable drug delivery system.

* * * * *